US011547366B2

(12) United States Patent
Sane et al.

(10) Patent No.: US 11,547,366 B2
(45) Date of Patent: Jan. 10, 2023

(54) METHODS AND APPARATUS FOR DETERMINING BIOLOGICAL EFFECTS OF ENVIRONMENTAL SOUNDS

(71) Applicant: Intel Corporation, Santa Clara, CA (US)

(72) Inventors: Monika S. Sane, Folsom, CA (US); David I. Poisner, Carmichael, CA (US); Yuri I. Krimon, Folsom, CA (US)

(73) Assignee: Intel Corporation, Santa Clara, CA (US)

(*) Notice: Subject to any disclaimer, the term of this patent is extended or adjusted under 35 U.S.C. 154(b) by 530 days.

(21) Appl. No.: 15/476,391

(22) Filed: Mar. 31, 2017

(65) Prior Publication Data
US 2018/0279962 A1 Oct. 4, 2018

(51) Int. Cl.
| | |
|---|---|
| *A61B 5/00* | (2006.01) |
| *A61B 5/021* | (2006.01) |
| *A61B 5/024* | (2006.01) |
| *A61B 5/08* | (2006.01) |
| *A61B 5/0531* | (2021.01) |
| *G16H 50/20* | (2018.01) |
| *G16H 50/70* | (2018.01) |

(Continued)

(52) U.S. Cl.
CPC ............ *A61B 5/7275* (2013.01); *A61B 5/021* (2013.01); *A61B 5/024* (2013.01); *A61B 5/0531* (2013.01); *A61B 5/0816* (2013.01); *A61B 5/7246* (2013.01); *A61B 5/7282* (2013.01); *G16H 15/00* (2018.01); *G16H 40/63* (2018.01); *G16H 50/20* (2018.01); *G16H 50/70* (2018.01); *A61B 5/0205* (2013.01)

(58) Field of Classification Search
CPC .... A61B 5/7275; A61B 5/7246; A61B 5/7282
See application file for complete search history.

(56) References Cited

U.S. PATENT DOCUMENTS 5,317,273 A * 5/1994 Hanson ................. H04R 29/00
324/602
8,347,326 B2 1/2013 Weitzenfeld et al.
(Continued)

OTHER PUBLICATIONS

Williams, Sarah, "Sounds you can't hear can still hurt your ears," Science (American Association for the Advancement of Science), Sep. 30, 2014, retrieved from [http://www.sciencemag.org/news/2014/09/sounds-you-cant-hear-can-still-hurt-your-ears] on Jun. 27, 2017, 9 pages.

*Primary Examiner* — Lynsey C Eiseman
*Assistant Examiner* — Amanda L Steinberg
(74) *Attorney, Agent, or Firm* — Hanley, Flight & Zimmerman, LLC

(57) ABSTRACT

Methods and apparatus for determining biological effects of environmental sounds are disclosed. An example apparatus includes a sound characteristic analyzer to identify a sound event based on audio data in an environment. The example apparatus includes a physiological data analyzer to identify a physiological event based on physiological response data collected from a user exposed to the sound event in the environment. The example apparatus includes a correlation identifier to identify a correlation between the sound event and the physiological event and a report generator to generate a report based on the correlation.

42 Claims, 4 Drawing Sheets

(51) Int. Cl.
  *G16H 40/63* (2018.01)
  *G16H 15/00* (2018.01)
  *A61B 5/0205* (2006.01)

(56) References Cited

U.S. PATENT DOCUMENTS

| | | | |
|---|---|---|---|
| 8,384,548 B2* | 2/2013 | Knopf | E04G 21/32 |
| | | | 340/5.1 |
| 8,867,764 B1* | 10/2014 | Wiggins | A61B 5/121 |
| | | | 381/314 |
| 9,503,829 B2 | 11/2016 | Baskaran et al. | |
| 9,928,848 B2* | 3/2018 | Cahill | G10L 21/0308 |
| 2003/0179887 A1 | 9/2003 | Cronin | |
| 2004/0018476 A1 | 1/2004 | LaDue | |
| 2004/0190729 A1* | 9/2004 | Yonovitz | G01H 3/14 |
| | | | 381/72 |
| 2008/0267416 A1* | 10/2008 | Goldstein | H04R 1/1091 |
| | | | 381/56 |
| 2009/0092261 A1* | 4/2009 | Bard | G06F 1/3287 |
| | | | 381/71.1 |
| 2009/0150919 A1 | 6/2009 | Lee et al. | |
| 2015/0172841 A1* | 6/2015 | Goldstein | H04R 29/008 |
| | | | 381/56 |
| 2015/0222989 A1* | 8/2015 | Labrosse | H04R 1/1083 |
| | | | 381/71.1 |
| 2015/0326965 A1* | 11/2015 | Sprague | H04R 25/65 |
| | | | 381/317 |
| 2016/0234607 A1* | 8/2016 | Krystek | H04R 25/305 |
| 2016/0317049 A1* | 11/2016 | LeBoeuf | G16H 50/30 |
| 2020/0228907 A1 | 7/2020 | Mishra et al. | |

\* cited by examiner

METHODS AND APPARATUS FOR DETERMINING BIOLOGICAL EFFECTS OF ENVIRONMENTAL SOUNDS

FIELD OF THE DISCLOSURE

This disclosure relates generally to environmental sound analysis and, more particularly, to methods and apparatus for determining biological effects of environmental sounds.

BACKGROUND

An individual is exposed to many different environmental sounds on a daily basis, including, for example, sounds generated by traffic, machines, music playing, people talking, etc. Some of the sounds the individual encounters in an environment are sustained. For example, an individual working in a factory is exposed to sounds generated by machinery for an extended period of time over the work day. Other sounds are sudden, such as a loud explosion when the individual walks by a construction site. Exposure to different sounds affects an individual physiologically and psychologically.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
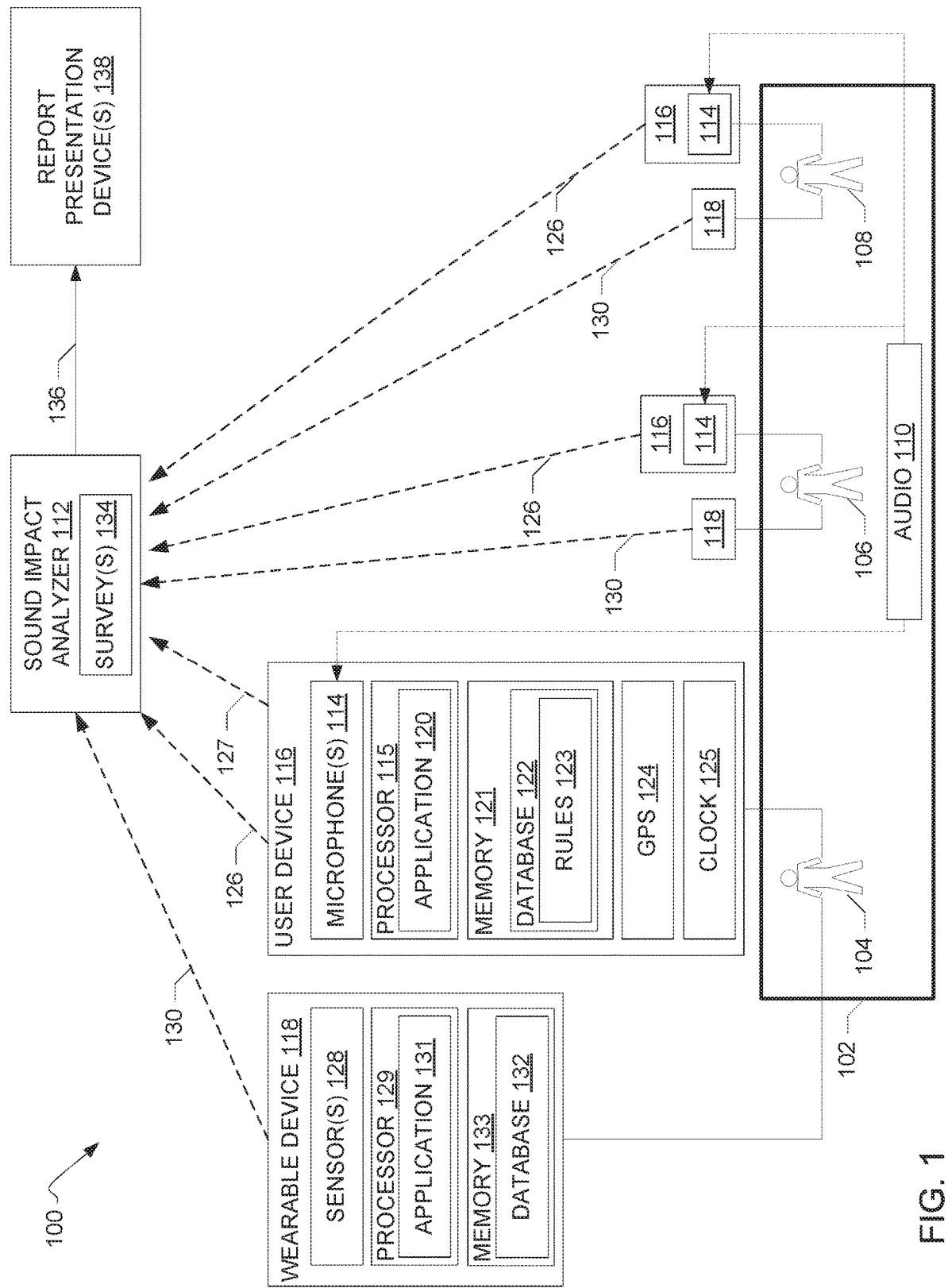
FIG. 1 illustrates an example system constructed in accordance with the teachings disclosed herein including a biological data collection device, an audio collection device for collecting environmental sounds, and a networked sound impact analyzer for determining the biological effects of the sounds.

On a daily basis, an individual is exposed to many different sounds emanating from different environments. For example, in a work environment such as a factory or office, the individual may be exposed to sounds generated by machinery, people talking, music playing, etc. When the individual is outside, the individual may be exposed to sounds generated by traffic, construction equipment, etc. In some examples, the individual may be exposed to infrasonic sounds, or sounds occurring at frequency levels below the human hearing range (e.g., below 20 Hz). Infrasonic sounds can stem from nature, such as earthquakes, or man-made sources, such as trucks, aircraft, etc. In some examples, the individual may be exposed to ultrasonic sounds, or sounds occurring at frequency levels above the human hearing range (e.g., above 20,000 Hz). Ultrasonic sounds can include certain animal whistles (e.g., dog whistles) or sonar emissions.

Exposure to different sounds—whether sustained, sudden, infrasonic, ultrasonic, etc.—may affect individuals physiologically and/or psychologically. Different individuals respond differently to different sounds. Characteristics of sound such as pitch, amplitude, duration, pattern, attack (e.g., a way in which a sound is initiated, where the sound of gunshot has a fast attack and the sounds of tearing a sheet of paper has a slow attack) can affect physical biological parameters such as heart rate and blood pressure. Further, individuals may have different psychological responses to sound. For example, a first individual may consider a sound to be noise (e.g., unwanted sound), while a second individual may consider the sound to be pleasant. Thus, physiological and/or psychological effects of sound on individuals can differ from no effect to, for example, hearing loss and/or stress.

Although some audio media players such as smartphones display warnings when a user raises the volume to alert the user to the risk of hearing damage, such warnings are based on decibel levels. Thus, such sound measurements do not account for other characteristics of sound, such as pattern and duration. Further, generic warnings based on decibel levels do not correlate sound with the physiological and/or psychological effects of the sound on the user. Moreover, such warnings do not account for different user responses to different sounds and, thus, are not user-specific.

Example systems and methods disclosed herein analyze audio collected from an environment and physiological response data collected from a user exposed to the environment. In some examples, the physiological response data is collected while the user is in the environment. In some examples, the physiological response data is additionally or alternatively collected after the user is removed from the environment. Based on the analysis of the audio and the physiological response data, examples disclosed herein correlate sound events with the physiological response data to identify the effects of sound on the user. Some examples identify effect(s) of specific sounds, such as an explosion, on the user's physiological response(s). Other examples identify effect(s) of sustained or repeated sounds on a user, such as daily exposure to machinery sounds in a factory, based on historical tracking of audio and physiological responses. Some examples combine survey data obtained from the user with the physiological response data to assess the effect(s) of the sound(s) on the user physiologically and psychologically.

Disclosed examples collect (e.g., record) audio content in an environment via a microphone associated with, for example, a smartphone, a wearable device, and/or a stand-alone speaker/audio sensor device (e.g., Amazon™ Echo™). The audio is wirelessly transmitted to a networked analyzer (e.g., a server, one or more processors, etc.) via an application (an app) executed on the microphone-enabled user device. Disclosed examples monitor a user's physiological responses such as heart rate, blood pressure, and/or respiration rate via one or more sensors of a wearable device worn by the user. The physiological response data is wirelessly transmitted to the analyzer. In some examples, the wearable device and the microphone-enabled device are the same device.

Based on the audio collected from the environment and the physiological data gathered from the user, examples disclosed herein determine correlations between the audio and the user's physiological response. Some such examples generate one or more outputs for presentation to the user via the user device application such as, for example, information about the user's hearing capacity and/or the user's daily exposure to the audio, personalized recommendations for audio level settings, etc. Some examples provide data to one or more third parties such as an authorized medical professional for tracking, for example, hearing loss.

In some examples, a plurality of users are located in an environment such as a factory from which one or more sounds are collected as audio data. Physiological data is collected from all or some of the users and transmitted to the analyzer. The analyzer identifies correlations between the sounds in the environment (e.g., in the building) and the users' physiological response data. Some such examples provide outputs to, for example, building managers with respect to the effects of sounds from equipment, elevators, etc. on the users. In some examples, substantially similar changes in physiological responses may be detected across users in substantially real-time corresponding to the detection of a specific (e.g., sudden) sound event. In such examples, the correlation between the similar changes in physiological responses across the users and the specific sound is used to determine that there has been a crowd-impacting event such as an explosion. Thus, disclosed examples may provide for sound event detection and/or customized warnings based on audio data and physiological data collected from one or more users.

FIG. 1 illustrates an example system 100 constructed in accordance with the teachings of this disclosure for determining the biological effect(s) of sound on a user exposed to audio in an environment. The example system 100 can be implemented in any environment 102. In the example system 100 of FIG. 1, a first user 104, a second user 106, and a third user 108 are exposed to sound(s) within the environment 102. Additional or fewer users can be present in the environment 102.

The environment 102 can be, for example, an indoor setting such as a building (e.g., a factory, an office building, a home, etc.) or an outdoor setting (e.g., an amusement park, a construction site, an airfield, etc.). In some examples, the environment 102 is based on a location of a particular user (e.g., one of the first, second, or third users 104, 106, 108). For example, the environment 102 can be defined by one or more locations that the first user 104 moves between, such as home, a city street, an office building, etc.

The user(s) 104, 106, 108 are exposed to audio 110 while in the environment 102. The audio 110 can include sound(s) generated by traffic, machines, voices, music, etc. In some examples, the audio 110 includes humanly audible sounds, infrasonic sounds (e.g., low-frequency sounds below the human hearing range) and/or ultrasonic sounds (e.g., high-frequency sounds above the human hearing range). In some examples, the audio 110 includes sudden sound(s) (e.g., a loud crash) or sustained sound(s) (e.g., sound(s) generated by a machine running for a duration of the work day). The audio 110 in the environment 102 can include one or more sound(s) having different or similar characteristics with respect to pitch, amplitude, duration, attack, pattern, etc.

In the example of FIG. 1, the audio 110 is collected (e.g., recorded) by a microphone-enabled device and transmitted to a sound impact analyzer 112. In the example of FIG. 1, the sound impact analyzer 112 is implemented by one or more cloud-based device(s) such as one or more servers, processor(s), and/or virtual machine(s). In other examples, some of the analysis performed by the sound impact analyzer 112 is implemented by the cloud-based device(s) and other parts of the analysis are implemented by processor(s) of one or more user device(s) (e.g., smartphones).

In the example of FIG. 1, physiological response data is collected from each of the users 104, 106, 108 and transmitted to the sound impact analyzer 112. For ease of discussion, the collecting of the audio 110 and the collection of the physiological response data from the users 104, 106, 108 may be discussed in connection with the first user 104 with the understanding that the same or similar description apply to the second user 106 and/or the third user 108 in substantially the same manner.

In the example of FIG. 1, one or more microphones 114 are disposed in the environment 102 to collect the audio 110. The microphone(s) 114 can be associated with a user device 116 (e.g., user device(s) of any or all of the first user 104, the second user 106, and/or the third user 108). The user device 116 can be implemented by a smartphone, a tablet, etc. In other examples, the user device 116 is a stand-alone speaker/audio sensor device located in the environment 102, such as the Amazon™ Echo™ or Google™ Home™. In some examples, the microphone(s) 114 are associated with wearable device(s) 118, such as a watch, glasses, a wearable walkie-talkie, etc. The wearable device(s) 118 may be worn by any or all of the users 104, 106, 108. In some examples, the microphone(s) 114 are implemented by a Bluetooth microphone associated with a Bluetooth-enabled user device. For illustrative purposes, the microphone(s) 114 are shown as associated with each of the user devices 116 in FIG. 1 but, in practice, each user device 116 need not have a microphone and/or the microphone(s) can be associated with a different device.

In the example of FIG. 1, the user device 116 includes a processor 115. The processor 115 executes a first user application 120. The first user application 120 instructs the microphone(s) 114 to collect the audio 110 in the environment 102. In some examples, the first user application 120 instructs the microphone(s) 114 to collect the audio 110 for a predefined time period, such as while the first user application 120 is running. In other examples, the first user application 120 instructs the microphone(s) 114 to collect the audio 110 based on one or more user inputs received via the user device 116 to start and stop the audio collecting.

The processor 115 of the user device 116 is in communication with a memory 121. In the illustrated example, the memory 121 stores a database 122. The database 122 includes one or more rules 123 with respect to the collection of the audio 110. For example, the rule(s) 123 identify one or more event(s) and/or threshold(s) that trigger recording of the audio 110. In some such examples, the microphone(s) may be "always on" in that they always collect audio. This audio may be buffered in the memory 121 temporarily. The audio may be discarded and/or overwritten unless an event occurs as defined in the rule(s) 123 (e.g., unless a threshold is satisfied). In some examples, the threshold includes an amplitude level. In such examples, the audio 110 exported to the sound impact analyzer 112 and/or preserved for such exportation if the audio 110 surpasses the threshold amplitude level. In other examples, the threshold is based on one or more other characteristics of the audio 110, such as a pattern of the sound and/or a duration of the sound. In some examples, the threshold for exporting and/or preserving the audio 110 for exporting is based on a location of the user 104, 106, 108 (e.g., as detected by a GPS 124 of the user device 116) or a time of day (e.g., as detected by a clock 125 of the user device 116). In some examples, the microphone(s) 114 may only collect audio when in the noted location(s) and/or during the noted time(s) of day (e.g., the microphone(s) 114 are not "always on" but instead are activated for audio collection only when the defined conditions are met). The thresholds can be set by the user 104, 106, 108 and/or a third party such as a medical professional. The rule(s) 123 can also include settings with respect to the duration of time the audio 110 should be recorded, a digital format for the recording, a time at which the data should be exported, an amount of data that is presented for exporting, etc.

The example first user application 120 of FIG. 1 generates an audio stream 126 based on the audio 110 collected by the microphone(s) 114 that is to be exported to the sound impact analyzer 112. In some examples, the audio stream 126 is stored in the memory 121 or a buffer. The example user device 116 of FIG. 1 is in communication (e.g., wireless communication) with the sound impact analyzer 112. The user device 116 may transmit the audio stream 126 to the sound impact sound impact analyzer 112 using any past, present, or future communication protocol. In some examples, the user device 116 transmits the audio stream 126 to the sound impact analyzer 112 in substantially real-time as the audio stream 126 is generated. In other examples, the user device 116 transmits the auto stream 126 to the sound impact analyzer 112 at a later time (e.g., based on one or more settings such as a preset time of transmission, an amount of data buffered, availability of WiFi, etc.).

In some examples, the user 104, 106, 108 provides one or more user inputs 127 via the first user application 120. The user input(s) 127 can include preferences with respect to, for example, the collection, buffering, storage, and/or recording of the audio stream(s) 126 by the user device 116. The user input(s) 127 can include data such as whether the corresponding user 104, 106, 108 is wearing or, more generally, associated with a noise reduction device (e.g., the user is wearing ear plugs, the user is located in a sound-proof room in the environment). In some examples, the first user application 120 periodically or aperiodically presents the user 104, 106, 108 with one or more surveys 134 such as whether he/she heard a specific sound collected by the microphone(s) 114 (e.g., based on a decibel level threshold defined by the rule(s) 123). The surveys 134 can include, for example, questions about the user's physiological responses to the sound(s), such as whether the user 104, 106, 108 was frightened. The surveys 134 can be generated by the first user application 120 and/or the sound impact analyzer 112. The user 104, 106, 108 can provide the user input(s) 127 via the user device 116 (e.g., via a display screen of the user device 116 or via another interface). In the example of FIG. 1, the user device 116 transmits the user input(s) 127 to the sound impact analyzer 112.

In the example of FIG. 1, each user 104, 106, 108 wears a wearable device 118. As disclosed herein, the wearable device 118 can be a watch, glasses, a wearable walkie-talkie, etc. The example wearable device 118 of FIG. 1 includes one or more sensors 128. The sensor(s) 128 measure one or more physiological parameters of the corresponding user 104, 106, 108, such as heart rate, blood pressure, arterial stiffness (e.g., as an index for blood pressure), skin conductivity, respiration rate, respiration pattern, etc. The sensor(s) 128 generate physiological response data 130 based on the measurements. In some examples, the sensor(s) 128 measure the physiological parameters while the corresponding user 104, 106, 108 wearing the device 118 is in the environment 102. In other examples, the sensor(s) 128 measure the physiological parameters after the user 104, 106, 108 has left environment 102. In some examples, the sensor(s) 128 measure the physiological parameters while the user 104, 106, 108 is in the environment 102 and for a period of time after the user leaves from the environment 102.

The example wearable device(s) 118 include a processor 129. The processor 129 of this example executes a second user application 131. The second user application 131 is used to control, for example, the collection of the physiological response data 130 via the sensor(s) 128 and/or the exportation of the data for the wearable device 118. The physiological response data 130 can be stored in a database 132 implemented by a memory 133 in communication with the processor 129.

The example wearable device 118 of FIG. 1 is in communication (e.g., wireless communication) with the sound impact analyzer 112 of FIG. 1. The example wearable device 118 transmits the physiological response data 130 to the sound impact analyzer 112. In some examples, the wearable device 118 transmits the physiological response data 130 to the sound impact analyzer 112 in substantially real-time as the physiological response data 130 is generated. In other examples, the wearable device 118 transmits the physiological response data 130 to the sound impact analyzer 112 at a later time (e.g., periodically and/or aperiodically based on one or more settings).

In some examples of the system 100 of FIG. 1, the wearable device 118 and the user device 116 are integrated into one device. For example, the processor 129 of the wearable device 118 can include the microphone(s) 114. The processor 129 of the wearable device can implement the first user application 120. In such examples, the wearable device 118 transmits the physiological response data 130, the audio stream 126, and/or the user input(s) 127 to the sound impact analyzer 112.

As illustrated in FIG. 1, the example sound impact analyzer 112 receives respective physiological response data 130 from the wearable device(s) 118 worn by the respective users 104, 106, 108. In some examples, the sound impact analyzer 112 receives also respective audio streams 126 from the user devices 116 associated with the different users 104, 106, 108 (e.g., smartphones). In other examples, the audio stream 126 is transmitted to the sound impact analyzer 112 via only one of the user devices 116 (e.g., the user device 116 associated with the first user 104). For example, if the first, second, and third users 104, 106, 108 are located in the same room, the audio stream 126 generated from the audio 110 may be collected by the microphone(s) 114 of the user devices 116 associated with all of the users 104, 106, 108. However, the audio stream 126 represents the audio to which all of the users 104, 106, 108 are exposed, so only one of the devices 116 need report the audio to the sound impact analyzer 112.

The example sound impact analyzer 112 analyzes the audio stream(s) 126 and the physiological response data 130 from the first, second, and/or third users 104, 106, 108 to correlate the physiological responses of the user(s) with sound event(s) in the audio stream(s) 126. For example, the sound impact analyzer 112 may correlate a change (e.g., an increased heart rate) detected in the physiological response data 130 collected from the user 104, 106, 108 over a time period with a sound event detected in the audio stream 126 (e.g., an increase in amplitude) over the same time period. In some examples, the sound impact analyzer 112 tracks changes in the physiological response data 130 compared to previously collected or historical physiological response data 130 for the user 104, 106, 108. In such examples, the sound impact analyzer 112 may correlate the changes in the physiological response data 130 to sustained or repeated exposure to sounds based on the data in the audio stream 126. In some examples, the sound impact analyzer 112 analyzes the physiological response data 130 for two or more of the first, second, and third users 104, 106, 108 relative to the audio stream(s) 126. In such examples, the sound impact analyzer 112 identifies the effect(s) of sound event(s) in the audio stream(s) 126 across two or more users based on, for example, similar changes identified in the physiological response data for the corresponding users. In some examples, the sound impact analyzer 112 receives user survey data collected from the user(s) 104, 106, 108. In some such examples, the sound impact analyzer 112 accounts for the psychological responses of the user(s) 104, 106, 108 with respect to identifying correlations between the audio 110 and the physiological response data 130.

In some examples, the sound impact analyzer 112 of FIG. 1 generates one or more surveys 134 based on the analysis of the audio stream(s) 126 and the physiological response data 130 from the first, second, and/or third user(s) 104, 106, 108. As disclosed above, in the example of FIG. 1, the survey(s) 134 are presented to the user(s) 104, 106, 108 via the user device(s) 116.

The example sound impact analyzer 112 generates one or more reports or instructions 136 based on the analysis of the audio stream(s) 126, the physiological response data 130 from the user(s) 104, 106, 108, and/or the user input(s) 127 in response to the survey(s) 134 indicative of psychological responses of the user(s) 104, 106, 108 to the sound(s) in the environment 102. The report(s) 136 can include, for example, personalized recommendations for audio levels for the user(s) 104, 106, 108 based on the physiological response data, alerts regarding danger(s) or potential ill effects of prolonged exposure to the audio 110, information regarding the user's hearing capacity, etc. In some examples, the report(s) 136 include information about noise sources in the environment 102 that may be causing certain physiological response(s) in the user(s) in the environment. For example, the report(s) 136 can indicate whether the user(s) 104, 106, 108 are experiencing adverse physiological responses to a machine that generates a sustained operational sound and is located in the same room as the user(s) 104, 106, 108. The report(s) 136 can indicate whether the user(s) 104, 106, 108 are experiencing adverse physiological responses to the sound(s) in the environment 102, such as stress and/or anxiousness. The report(s) 136 can be presented in, for example, a visual format, an audio format, and/or another format (e.g., as a vibrating alert).

In some examples, the report(s) 136 include one or more instructions to be executed by the sound impact analyzer 112 or one or more other processors (e.g., the processor 115 of the user device 116, the processor 129 of the wearable device 118). For example, the report(s) 136 can include instruction(s) for an audio playing device in the environment 102 to automatically reduce a volume at which the audio 110 is played by the device in view of the physiological and/or psychological effects of sound exposure on the user(s) 104, 106, 108.

In the example system 100 of FIG. 1, the sound impact analyzer 112 is in communication with one or more report presentation devices 138. The report presentation device(s) 138 can include the user device(s) 116 and/or the wearable device(s) 118 associated with the user(s) 104, 106, 108 (e.g., display screen(s) of the device(s) 116, 118). In some examples, the report presentation device(s) 138 include user devices (e.g., tablets, smartphones, a personal computer) associated with a third party authorized to receive the report(s) 136, such as a medical professional, a parent, a building manager (e.g., of a factory building, an employer, etc.). In examples where the report(s) 136 include instruction(s) for execution, the report presentation device(s) 138 may execute the instructions to, for example, reduce sound in the environment.

Figure 2:
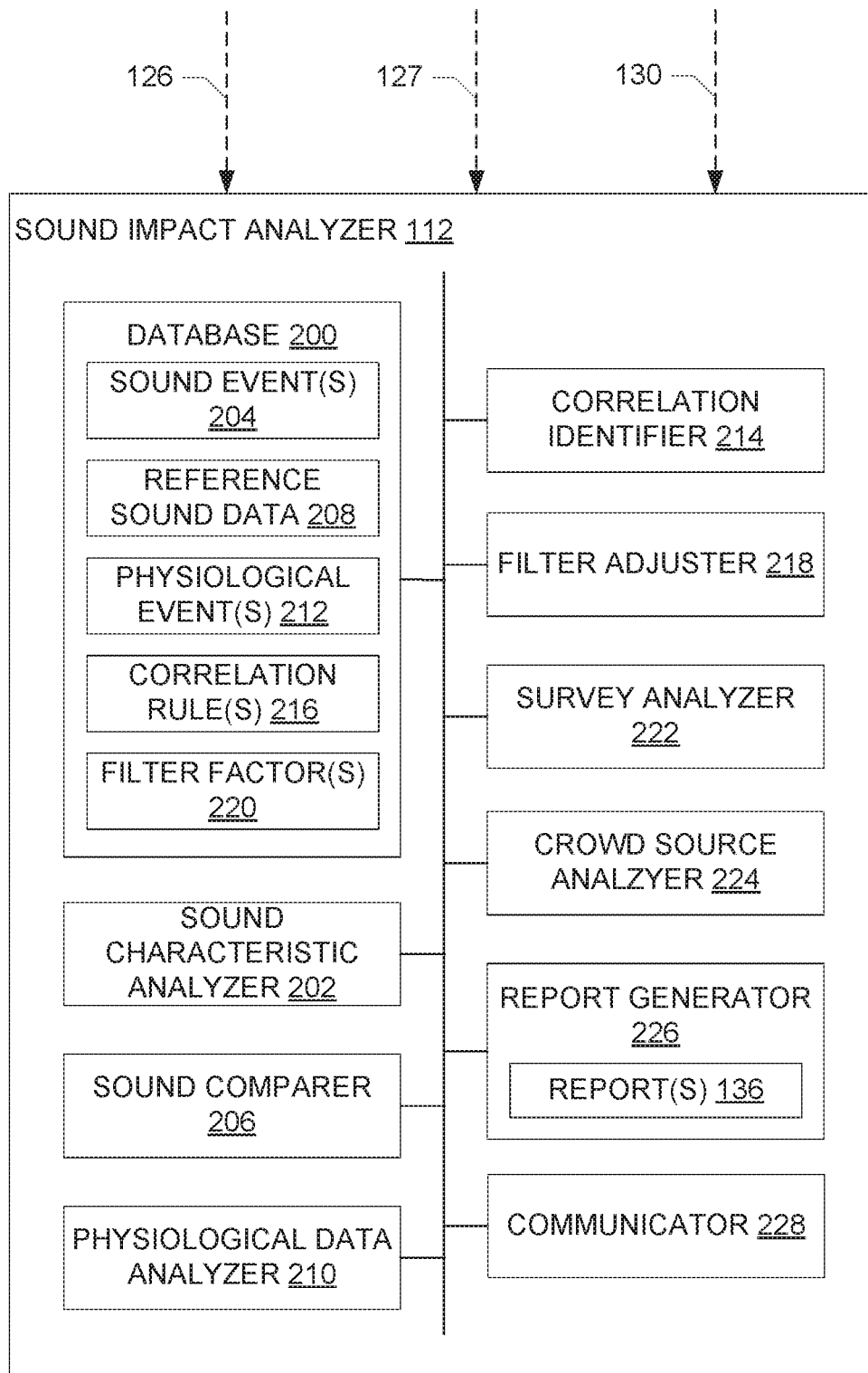
FIG. 2 is a block diagram of an example implementation of the sound impact analyzer of FIG. 1.

FIG. 2 is a block diagram of an example implementation of the example sound impact analyzer 112 of FIG. 1. As mentioned above, the example sound impact analyzer 112 is constructed to correlate physiological and/or psychological responses of a user (e.g., the first, second, and/or third users 104, 106, 108 of FIG. 1) with sound events in the audio stream(s) 126 representing sound(s) occurring in the environment 102. In the example of FIG. 2, the sound impact analyzer 112 is implemented by one or more servers and/or processor(s) located remotely from the users. In some examples, the sound impact analyzer 112 is implemented by one or more virtual machines in a cloud-computing environment. In other examples, the sound impact analyzer 112 is implemented by one or more of the processor 115 of the user device 116 and/or the processor 129 of the wearable device 118. In other examples, some of the sound impact analysis is implemented by the sound impact analyzer 112 (e.g., via a cloud-computing environment) and one or more other parts of the analysis is implemented by the processor 115 of the user device 116 and/or the processor 129 of the wearable device 118.

The example sound impact analyzer 112 of FIG. 2 includes a database 200. In other examples, the database 200 is located external to the sound impact analyzer 112 in a location accessible to the analyzer. As disclosed above, the audio stream(s) 126 corresponding to the audio 110 occurring in the environment 102 of FIG. 1 are transmitted to the sound impact analyzer 112. Similarly, the physiological response data 130 collected from the user is also transmitted to the sound impact analyzer 112. Also, in some examples, the user input(s) 127 in response to the survey(s) 134 (e.g., data indicative of physiological responses of the user) are transmitted to the sound impact analyzer 112. The database 200 stores the audio stream(s) 126, the physiological response data 130, and the user input(s) 127. In some examples, the database 200 stores the audio stream(s) 126 and/or the physiological response data 130 over time to generate historical audio data and/or historical physiological data, respectively.

The example sound impact analyzer 112 of FIG. 2 includes a sound characteristic analyzer 202. The sound characteristic analyzer 202 receives and/or otherwise retrieves the audio stream(s) 126 and processes the audio data included in the stream(s). The sound characteristic analyzer 202 can perform one or more operations on the audio data such as filtering the raw signal data, removing noise from the signal data, converting the signal data from analog data to digital data, converting time domain audio data into the frequency spectrum (e.g., via Fast Fourier processing (FFT)) for spectral analysis, and/or analyzing the data. In some examples, the audio data is converted from analog to digital before being delivered to the sound impact analyzer 112.

The example sound characteristic analyzer 202 of FIG. 2 analyzes the audio data of the audio stream(s) 126 with respect to one or more characteristics of sound(s) in the audio stream(s) 126, such as amplitude, frequency, pitch, duration, and/or attack. The sound characteristic analyzer 202 detects, for example, changes in the data with respect to one or more of the sound characteristics. For example, the sound characteristic analyzer 202 identifies change(s) in amplitude if a sound represented in the audio content stream data. As another example, the sound characteristic analyzer 202 identifies change(s) in pitch over time of sound(s) in the audio data. As another example, the sound characteristic analyzer 202 may detect an increase or decrease in a duration of a characteristic or event in the audio data (or a portion thereof) relative to, for example, previously collected audio data. The sound characteristic(s) (e.g., amplitude, pitch, duration, etc.) analyzed by the sound characteristic analyzer 202 can be defined by one or more user inputs.

Based on the analysis of the audio stream(s) 126, the example sound characteristic analyzer 202 identifies one or more sound events 204 in the audio stream(s) 126. In some examples, the sound characteristic analyzer 202 identifies a sound event 204 based on a change in one or more characteristics of the sound(s) represented in the audio data, such as an increase in amplitude for a period of time followed by a decrease in amplitude. In other examples, the sound characteristic analyzer 202 identifies a sound event 204 based on the characteristics of the audio data relative to previously identified sound event(s) 204. The sound event(s) 204 can include a discrete sound event (e.g., an increase in amplitude followed by a decrease in amplitude within a few seconds) or a sound event occurring over, for example, a duration of the time period for which the audio 110 is collected.

The sound impact analyzer 112 of the illustrated example includes a sound comparer 206. The sound comparer 206 may be implemented by a comparator or a processor programmed to perform a comparison. The sound comparer 206 compares the sound event(s) 204 of the audio stream(s) 126 to predefined or reference sound data 208 for one or more sounds. In the example of FIG. 2, the reference sound data 208 is stored in the database 200.

The sound comparer 206 compares the sound event(s) 204 of the audio stream(s) 126 to the reference sound data 208 to determine if, for example, the sound event(s) 204 in the audio 110 are sound event(s) to which the user has been previously exposed. For example, the sound comparer 206 can identify a sound event 204 in the audio streams(s) 126 as an expected sound event for the environment 102, such as traffic sounds for an outside environment or machine sounds for a factory environment. Thus, the reference sound data 208 provides a profile of expected or typical sound events for a given environment. In some examples, the reference sound data 208 is updated with known sound event(s) based on analysis of the audio stream(s) 126 collected over time.

The example sound impact analyzer 112 includes a physiological data analyzer 210. The physiological data analyzer 210 receives and/or otherwise retrieves the physiological response data 130 collected by the sensor(s) 128 and processes the data. The physiological data analyzer 210 can perform one or more operations on the physiological response data 130 such as filtering the raw signal data, removing noise from the signal data, converting the signal data from analog data to digital data, and/or analyzing the data.

The example physiological data analyzer 210 analyzes the physiological response data 130 collected from the user (e.g., the first user 104, the second user 106, and/or the third user 108) to identify characteristics of and/or changes in the physiological response data 130. For example, the physiological data analyzer 210 can analyze heart rate data collected from the user to determine a resting heart rate for the user and/or to identify changes (e.g., sudden or abrupt changes and/or gradual changes) in the user's heart rate. In some examples, the physiological data analyzer 210 compares the heart rate data to previously collected heart rate data for the user (e.g., previously collected physiological response data 130 stored in the database 200) to identify changes in the user's heart rate data over time. The physiological data analyzer 210 can analyze physiological response data 130 generated by the sensor(s) 128 from measurements of other physiological parameters such as blood pressure, respiration rate, skin conductivity, etc.

Based on the analysis of the physiological response data 130, the physiological data analyzer 210 generates one or more physiological events 212. In the example of FIG. 1, the physiological events 212 are stored in the database 200 (e.g., a database of physiological event(s) 212). In some examples, the physiological event(s) 212 are based on discrete events in the physiological response data 130, such as a sudden increase in heart rate relative to a prior (e.g., the resting) heart rate for the user followed by a return to the user's previous heart rate. In other examples, the physiological event(s) 212 are indicative of long-term or delayed change(s) in the physiological response data 130. Such long term changes are detected over time. An example of such long term change is a gradual increase in the user's resting heart rate (i.e., beats per minutes when the user is awake, substantially relaxed, and not ill). In some examples, the physiological event(s) 212 include short-term physiological events and long-term physiological events for one or more physiological parameters (e.g., heart rate, blood pressure, etc.).

The example sound impact analyzer 112 of FIG. 2 includes a correlation identifier 214. In the illustrated example, the correlation identifier 214 determines one or more correlations between the sounds event(s) 204 identified by the sound characteristic analyzer 202 and the physiological event(s) 212 identified by the physiological data analyzer 210. In some examples, the correlation identifier 214 uses one or more algorithms or correlation rules 216 stored in the database 200 to identify correlation(s) between the sound event(s) 204 and the physiological event(s) 212. The correlation rule(s) 216 can be defined by one or more user inputs and/or developed automatically over time based on a supervised or unsupervised machine learning algorithm. The correlation rule(s) 216 can include, for example, known correlations (e.g., a sudden, loud sound raises a user's heart rate) or weighing factors (e.g., a rule that more weight should be given to sound event(s) having a fast attack as compared to a slow attack).

For example, the sound characteristic analyzer 202 can identify a first sound event 204 indicating an increase in an amplitude of the audio 110 followed by a decrease in the amplitude at a first time $T_1$. Also, the physiological data analyzer 210 can identify a first physiological event 212 indicating an increase in the user's heart rate followed by a decrease in the user's heart rate (e.g., a return to a prior heart rate). The physiological data analyzer 210 can determine that the first physiological event 212 occurs at the first time $T_{1+n}$, where n is an increment of time (such as one second). Based on the identification of the first sound event 204 occurring at the first time $T_1$ and the first physiological event 212 occurring at the first time $T_{1+n}$, the correlation identifier 214 determines that there is a correlation (e.g., a causal connection) between the first sound event 204 (e.g., the increase in amplitude) and the first physiological event 212 (e.g., the increase in heart rate). In some examples, the correlation identifier 214 identifies a correlation between the first sound event 204 and the first physiological event 212 if the first physiological event 212 occurs within a threshold time of the first sound event 204 (e.g. $T_{1+n}$) as defined by the correlation rule(s) 216. The increment/threshold time n may be different for different types of sound increments (e.g., milliseconds later in the context of a sudden, loud noise or sound event, or within a 24-hour period of the occurrence in the case of a substantial sound event).

In some examples, the sound event(s) 204 represent sound(s) to which the user is repeatedly exposed to (e.g., every day) and/or is exposed to over a duration of time surpassing a threshold (e.g., longer than an hour, longer than seven hours). In such examples, the correlation identifier 214 evaluates the physiological event(s) 212 with respect to the cumulative exposure of the user to the sound event(s) 204.

For example, the first sound event 204 can represent a sound that occurs repeatedly within a first time period $T_1$ (e.g., an eight-hour time period). The first sound event 204 can be based on, for example, the sound characteristic analyzer 202 detecting data indicative of a high-pitch sound occurring repeatedly in the audio stream(s) 126. A first physiological event 212 can indicate an increase in the user's heart rate (e.g., based on historical physiological response data 130) during the first period $T_1$. A second physiological event 212 can indicate an increase in the user's heart rate relative to, for example, a resting heart rate for the user during a second time period $T_2$ different from the first time period $T_1$. The second time period $T_2$ can correspond to time when the user has departed the environment 102 but the physiological response data 130 is being collected from the user.

In such examples, the example correlation identifier 214 of FIG. 2 may identify a first correlation between the first sound event 204 and the first physiological event 212. The correlation identifier 214 can identify the first correlation based on, for example, the occurrence of the first sound event 204 and the first physiological event 212 during the first time period $T_1$. The first correlation can indicate that the user has a physiological response (e.g., a sustained increased heart rate) due to the repeated exposure to the first sound event 204 (e.g., the high pitch sound event) during the first time period $T_1$ (e.g., the eight-hour time period).

Also, in such examples, the example correlation identifier 214 may identify a second correlation between the first sound event 204 and the second physiological event 212. For example, the correlation identifier 214 may evaluate the second physiological event 212 relative to other sound events 204 occurring during the first time period $T_1$ and/or the second time period $T_2$ to determine if the second physiological event 212 is related to another sound event. The correlation identifier 214 may evaluate other physiological events 212 occurring during the first and/or second time periods $T_1$, $T_2$ relative to the first sound event 204 and/or other sound events 204. In some examples, the correlation identifier 214 gives more weight to the repeated nature of the first sound event 204 during the first time period $T_1$ as compared to other sound events that may only occur once during the first time period $T_1$ or the second time period $T_2$. Based on the analysis of the second physiological event 212 relative to other sounds events 204, the analysis of other physiological events 212 for the user, and/or the weight given to the repeated nature of the first sound event 204, the correlation identifier 214 determines that there is a correlation between the first sound event 204 and the second physiological event 212. Thus, the correlation identifier 214 can identify physiological effects of exposure to sound event(s) 204 that may appear in the physiological response data 130 at a time after the occurrence(s) of the sound event(s) 204 and/or after the user is removed from the environment.

In some examples, the first sound event 204 occurs repeatedly during the first time period $T_1$ and each time the user is in the environment 102 (e.g., five days a week). In some such examples, the correlation identifier 214 determines that the second physiological event 212 occurs each time or substantially each time the user is exposed to the first sound event 204. The correlation identifier 214 may determine that there is a correlation between the first sound event 204 and the second physiological event 212 in view of the repeated occurrence of the second physiological event 212 when the first sound event 204 occurs over multiple data collection periods. Thus, the correlation identifier 214 determines cumulative, long-term, and/or delayed physiological effects of exposure to the sound event(s) on the user, such as increased heart rate (which may be an indicator of stress) for a user who works in a factory with loud machinery.

As another example, based on the characteristics of sound events 204 identified by the sound characteristic analyzer 202 (e.g., attack, amplitude, duration) and the reference sound data 208, the sound comparer 206 may determine that the user is exposed to loud voices as compared to average voice levels and more frequently than expected. The physiological data analyzer 210 may identify physiological events 212 for the user indicative of an increased resting heart rate over time. The correlation identifier 214 may determine a correlation between the sound events 204 and the physiological events 212 indicative of the effects of the loud voices on the user.

In some examples, the correlation identifier 214 of FIG. 2 implements one or more machine learning algorithms (e.g., supervised learning algorithms). For example, the correlation identifier 214 can learn physiological responses to one or more sounds events 204 for a user based on the analysis of the physiological response data 130 collected from the user over time. In some examples, the correlation identifier 214 aggregates physiological responses to one or more sound events collected from two or more users (e.g., the first user 104, the second user 106, and/or the third user 108 of FIG. 1). Based on the aggregated data, the example correlation identifier 214 identifies trend(s) in the physiological response(s) of user(s) to different sounds event(s) 204. In some examples, the correlation identifier 214 uses the trend(s) to determine correlation(s) between the sound event(s) 204 having similar characteristics as the sound event(s) for which the trend(s) were identified and the physiological event(s) 212 for one or more users. Thus, the correlation identifier 214 identifies correlation(s) based on machine learning algorithms with respect to the sound event(s) 204 and the physiological event(s) 212. In some examples, the correlation identifier 214 assigns strength level(s) to the correlation(s) identified between the sound event(s) and the physiological event(s) 212 (e.g., a strong correlation, a probable correlation).

The example sound impact analyzer 112 of FIG. 2 includes a filter adjuster 218. In some examples, the filter adjuster 218 evaluates the analysis of the sound event(s) 204 and the physiological event(s) 212 performed by the correlation identifier 214 in view of one or more filter factors 220 stored in the database 200. The filter adjuster 218 determines if the analysis should account for one or more filter factors 220. The filter factor(s) 220 can be defined based on one or more user inputs. The filter analyzer 212 can consider, for example, attenuation, gain, etc. with respect to the audio data corresponding to the sound event(s) 204.

For example, a user input 127 may be received at the sound impact analyzer 112 (e.g., via the first user application 120) indicating that the user from which the physiological response data 130 is collected is wearing a noise reduction device such as ear plugs. Based on a filter factor 220, the filter adjuster 218 recognizes that the ear plugs cause the user to hear sound differently (e.g., at a reduced volume) than the sound characteristics reflected in the audio stream 126 from the microphone(s) 114. In such examples, the filter adjuster 218 communicates with the correlation identifier 214 regarding the impact of the noise reduction device, such as reduced decibel levels from the user's perspective. The example correlation identifier 214 considers the use of the noise reduction device by the user when determining the correlation(s) between the sound event(s) 204 and the physiological event(s) 212. For example, the correlation identifier 214 may determine that there is no correlation between a sound event 204 and a physiological event 212 because the user was wearing ear plugs and, thus, was not exposed to, or had limited exposure to, the sound event 204.

As another example, a first audio stream 126 collected by a first microphone 114 of a first user device 116 (e.g., a smartphone) may include audio data having a decibel level of 84 db. A second audio stream 126 collected by a second microphone 114 of a second user device 116 (e.g., a stand-alone speaker/audio sensor device (e.g., Amazon™ Echo™)) may include audio data having a decibel level of 89 db. In this example, the first audio stream 126 and the second audio stream 126 are generated based on the same audio 110 for the same time period. The example filter adjuster 218 determines that the decibel level of the audio data collected by the first user device 116 is less than the decibel level of the audio data collected by the second user device 116. Thus, the filter adjuster 218 determines that the audio data of the first audio stream 126 is attenuated relative to the audio data of the second audio stream 126. For example, the first user device 116 (e.g., the smartphone) may be disposed in the user's pocket, a purse, etc. and, thus, sounds detected by the microphone 114 may be muted as compared to the sound detected by the second user device 116 (e.g., the stand-alone speaker/audio sensor device).

In other examples, the filter adjuster 218 determines that the first audio stream 126 generated by the first user device 116 includes attenuated data based on a comparison of the sound characteristics identified by the sound characteristic analyzer 202 for the audio data of the first audio stream 126 to the reference sound data 208 stored in the database 200. For example, the filter adjuster 218 can determine that the audio data is attenuated based a comparison of the decibel level for the audio data to an expected decibel level in the reference sound data 208.

If the filter adjuster 218 determines that the audio data in the first audio stream 126 is attenuated, the filter adjuster 218 communicates with the correlation identifier 214. The correlation identifier 214 accounts for the fact that the user may be exposed to the audio 110 at, for example, a higher decibel level than reflected in the first audio stream 126 when determining correlations between the sound event(s) 204 and the physiological event(s) 212. Thus, the filter adjuster 218 improves accuracy and/or reduces errors in the analysis of the sound event(s) 204 and the physiological event(s) 212 by the correlation identifier 214 by accounting for factors such as placement of the microphone relative to the user and/or the use of a noise reduction device by the user.

The example sound impact analyzer 112 of FIG. 2 includes a survey analyzer 222. The survey analyzer 222 analyzes the survey data included in the user input(s) 127 collected from the user (e.g., via the user device 116) in response to the survey(s) 134. As disclosed above, the user input(s) 127 can include inputs from user about the whether the user heard one or more sounds and/or the user's psychological response to the sound(s) (e.g., level of fright). The survey analyzer 222 tracks changes in the user's responses over time. For example, the survey analyzer 222 may determine that the user's hearing abilities have changed based on an indication that the user no longer hears a sound he or she previously indicated he or she heard. In other examples, the survey analyzer 222 determines that the user's psychological response to the sound has changed based on changes in the user's responses regarding fright levels.

In some examples, the survey analyzer 222 communicates with the correlation identifier 214 to assess or verify the correlations identified by the correlation identifier 214 in view of survey responses. For example, the correlation identifier 214 and/or the survey analyzer 222 may confirm a correlation between a sound event 204 including an increase in amplitude and a physiological event 212 indicating an increase in the user's heart rate based on survey respond data stating that the user was frightened when he or she heard the sound corresponding to the sound event 204.

In some examples, the survey analyzer 222 adapts future questions for the survey(s) 134 based on the user's responses. For example, if the user indicates that he or she did not hear a sound having a low frequency, such as a humming noise, the survey analyzer 222 refrains from generating questions regarding the sound in future survey(s) 134. In some examples, the adjustment of the survey questions by the survey analyzer 222 is used to track changes in the user's hearing ability and/or psychological responses to the audio 110.

The example sound impact analyzer 112 of FIG. 2 includes a crowd source analyzer 224. As disclosed above, in some examples, the example sound impact analyzer 112 receives audio stream(s) 126 and physiological response data 130 for a plurality of users associated with the environment 102 (e.g., the first user 104, the second user 106, and/or the third user 108). In some examples, the audio stream(s) 126 and the physiological response data 130 are received in substantially real-time. In such examples, the sound impact analyzer 112 analyzes the audio stream(s) 126 and the physiological response data 130 received from the users in substantially real-time to identify specific sound event(s) causing similar physiological responses in the users. In other examples, the analysis is not done in real-time or substantially real-time.

For example, based on the audio streams 126, the sound characteristic analyzer 202 may detect a sound event 204 based on one or more characteristics of the audio data, such as attack, duration, amplitude, etc. Also, the sound comparer 206 may determine that the sound event is not a sound typically occurring in the environment 102 based on a comparison of the sound event 204 to the reference sound data 208. Also, the physiological data analyzer 210 may identify a physiological event 212 occurring in two or more of the users. The physiological event 212 identified for the users may be based on one or more similar changes in one or more physiological parameters, such as an increase in heart rate and/or respiration rate.

Based on the sound event 204 and the physiological event 212 identified from data collected from a plurality of users, the crowd source analyzer 224 may determine that there has been a crowd-impact event affecting the users. Based on the comparison of the sound event 204 to the reference sound data 208 by the sound comparer 206, the crowd source analyzer 224 may determine that the crowd-impact event is a non-typical audio event for the environment, such as an explosion. Thus, the crowd source analyzer 224 can identify events affecting a plurality of the users in the environment in substantially real-time. Additionally or alternatively, the crowd source analyzer 224 can identify trends in the population with respect to physical and/or emotion health and use those trends to recommend changes in the environment to reduce any negative effects.

The example sound impact analyzer 112 of FIG. 2 includes a report generator 226. Based on the correlations identified by the correlation identifier 214, the analysis of the survey responses by the survey analyzer 222, and/or the detection of a crowd-impact event and/or trends by the crowd source analyzer 224, the report generator 226 generates one or more of the reports 136 for output by the sound impact analyzer 112.

For example, the report(s) 136 can include metrics regarding a user's exposure to different sounds and/or recommendations for audio levels of devices such as televisions. The recommendations can be based on the physiological impact of other sounds on the user in view of the correlations identified by the example correlation identifier 214. The recommendations can include preventive measures, such as a recommendation to lower television volume levels at night in view of prolonged exposure to machine sounds during the day and/or the user of ear protection equipment.

In some examples, the report(s) 136 include data regarding sound-generating sources in the environment 102. For example, the report(s) 136 can identify noise sources in a building (e.g., elevators, equipment) based on the correlations between sound event(s) detected in the building and physiological events detected in multiple users indicative of, for example, a trend in stress (e.g., increase heart rate). In some examples, specific noise sources are identified based on data such as a location of the user (e.g., based on GPS data) relative to the sources generating the sound event(s) 204.

In some examples, the report(s) 136 include data regarding the user's hearing capabilities and/or other physiological parameters (e.g., heart rate, etc.). For example, the report(s) 136 can include data regarding the user's exposure to sound over time and the user's responses to survey questions with respect to whether he or she heard the sound, his or her reaction to the sound, etc. As another example, the report(s) 136 can include indicators that the user is experiencing stress due to exposure to sound(s) based on analysis of heart rate data, blood pressure, respiration, etc. The report(s) 136 may be shared with, for example, the user and/or authorized medical personnel.

In some examples, the report(s) 136 include alerts to authorized personnel such as a building managers or law enforcement when the crowd source analyzer 224 detects a crowd-impact event such as an explosion, loud crash, etc. Thus, the example sound impact analyzer 112 can be used to provide data in, for example, emergency situations based on real-time analysis of audio data. In other examples, the report(s) 136 can be sent to government agencies, physicians, researchers, etc. to facilitate public health studies, OSHA regulations, and/or other activities.

In some examples, report generator 226 generates instructions to be executed by one or more processors (e.g., the processor 115 of the user device 116, the processor 129 of the wearable device 118, the sound impact analyzer 112). For example, the report(s) 136 can include instruction(s) for one or more sound generating devices (e.g., machines) in the environment 102 to reduce sound in the environment by automatically reducing and/or ceasing operations. As another example, the report generator 226 can generate instruction(s) for an audio playing device in the environment to automatically reduce an amplitude or decibel level at which the device(s) play the audio 110. In examples where the crowd source analyzer 224 identifies the occurrence of a crowd-impact event such as an explosion, the report generator 226 may automatically generate a request for law enforcement assistance, employer assistance, etc.

The report(s) 136 can include instruction(s) to automatically place an order for noise protection devices such as ear plugs or noise reduction head phones for the user(s) from an online source (e.g., Amazon™) or a local supplier to protect the user. Such instruction(s) can be executed by the sound impact analyzer 112 or any other processor (e.g., the processor 115 of the user device 116)

The example sound impact analyzer of FIG. 2 includes a communicator 228. The communicator 228 communicates with the report presentation device(s) 138 (e.g., the user device(s) 116 of FIG. 1) to deliver the report(s) 136 to local or remote report presentation device(s) 138 for display, storage, and/or further analysis to assess multiple environments to facilitate an industry-wide study, etc. The communicator 228 communicates with the report presentation device(s) 138 to execute the instruction(s) in the report(s) 136, such as instructions to reduce or end operation of a machine to reduce sound in the environment.

In some examples, the communicator 228 executes one or more of the instructions generated by the report generator 226. For example, in view of the detection of a crowd-impact event (e.g., an explosive sound) by the crowd source analyzer 224, the communicator 228 can automatically transmit a request for law enforcement assistance or employer assistance to the environment. As another example, the communicator 228 can automatically place an order for noise reduction device(s) (e.g., noise reduction headphones, ear plugs, noise insulating materials) from an online or local supplier to protect the user(s).

While an example manner of implementing the example sound impact analyzer 112 is illustrated in FIGS. 1 and 2, one or more of the elements, processes and/or devices illustrated in FIGS. 1 and 2 may be combined, divided, re-arranged, omitted, eliminated and/or implemented in any other way. Further, the example database 200, the example sound characteristic analyzer 202, the example sound comparer 206, the example physiological data analyzer 210, the example correlation identifier 214, the example correlation identifier 214, the example filter adjuster 218, the example survey analyzer 222, the example crowd source analyzer 224, the example report generator 226, the example communicator 228 and/or, more generally, the example sound impact analyzer 112 of FIGS. 1 and 2 may be implemented by hardware, software, firmware and/or any combination of hardware, software and/or firmware. Thus, for example, any of the example database 200, the example sound characteristic analyzer 202, the example sound comparer 206, the example physiological data analyzer 210, the example correlation identifier 214, the example correlation identifier 214, the example filter adjuster 218, the example survey analyzer 222, the example crowd source analyzer 224, the example report generator 226, the example communicator 228 and/or, more generally, the example sound impact analyzer 112 of FIGS. 1 and 2 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example database 200, the example sound characteristic analyzer 202, the example sound comparer 206, the example physiological data analyzer 210, the example correlation identifier 214, the example correlation identifier 214, the example filter adjuster 218, the example survey analyzer 222, the example crowd source analyzer 224, the example report generator 226, the example communicator 228 and/or, more generally, the example sound analyzer 112 of FIGS. 1 and 2 is/are hereby expressly defined to include a non-transitory computer readable storage device or storage disk such as a memory, a digital versatile disk (DVD), a compact disk (CD), a Blu-ray disk, etc. storing the software and/or firmware. Further still, the example sound impact analyzer 112 of FIGS. 1 and 2 may include one or more elements, processes and/or devices in addition to, or instead of, those illustrated in FIGS. 1 and 2, and/or may include more than one of any or all of the illustrated elements, processes and devices.

Figure 3:
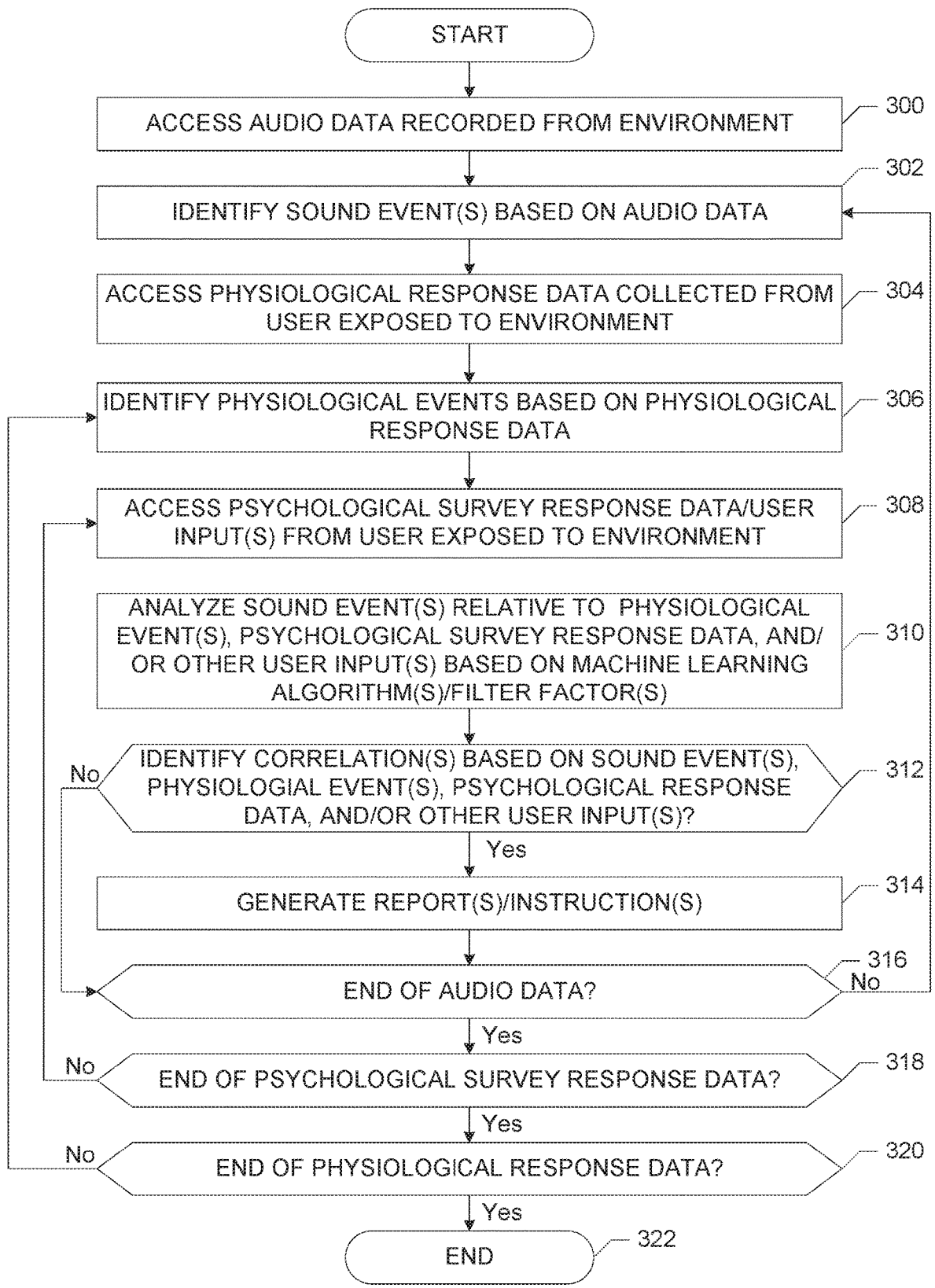
FIG. 3 is a flowchart representative of example machine readable instructions that may be executed to implement example systems of FIGS. 1 and/or 2.

A flowchart representative of example machine readable instructions for implementing the example system 100 of FIGS. 1 and 2 is shown in FIG. 3. In this example, the machine readable instructions comprise a program for execution by one or more processors such as the processor 112 shown in the example processor platform 400 discussed below in connection with FIG. 4. The program may be embodied in software stored on a non-transitory computer readable storage medium such as a CD-ROM, a floppy disk, a hard drive, a digital versatile disk (DVD), a Blu-ray disk, or a memory associated with the processor 112, but the entire program and/or parts thereof could alternatively be executed by a device other than the processor 112 and/or embodied in firmware or dedicated hardware. Further, although the example program is described with reference to the flowchart illustrated in FIG. 3, many other methods of implementing the example system 100 and/or components thereof may alternatively be used. For example, the order of execution of the blocks may be changed, and/or some of the blocks described may be changed, eliminated, or combined.

As mentioned above, the example processes of FIG. 3 may be implemented using coded instructions (e.g., computer and/or machine readable instructions) stored on a non-transitory computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term non-transitory computer readable storage medium is expressly defined to include any type of computer readable storage device and/or storage disk and to exclude propagating signals and to exclude transmission media. As used herein, "non-transitory computer readable storage medium" and "non-transitory machine readable storage medium" are used interchangeably.

FIG. 3 is a flowchart of example machine-readable instructions that, when executed, cause the example sound impact analyzer of FIGS. 1 and/or 2 to identify correlation(s) between sound(s) in an environment (e.g., the environment 102 of FIG. 1) and physiological response data collected from a user (e.g., the first user 104, the second user 106, and/or the third user 108 of FIG. 1) exposed to the environment. In the example of FIG. 3, the physiological response data can be collected via sensor(s) 128 of the wearable device 118 of FIG. 1. The sound(s) can be collected by microphone(s) 114 (e.g., the microphone(s) of the user device(s) 116 and/or the wearable device(s) 118 of FIG. 1). The example instructions of FIG. 3 can be executed by the sound impact analyzer 112 of FIGS. 1 and/or 2.

The example sound characteristic analyzer 202 of the sound impact analyzer 112 of FIG. 2 accesses the audio stream(s) 126 including audio data collected from the environment (block 300). The audio stream(s) 126 are generated by collecting sounds in the environment via the microphone(s) 114 (e.g., of the user device(s) 116 and/or the wearable device(s) 118). The audio stream(s) 126 can include, for example, audio data corresponding to traffic sounds, machine operations, etc.

The example sound characteristic analyzer 202 identifies sound event(s) 204 based on the audio data in the audio stream(s) 126 (block 302). For example, the sound characteristic analyzer 202 identifies one or more sound characteristics, such as amplitude, frequency, pitch, duration, and/or attack. Based on the sound characteristics and/or changes in the sound characteristics in the audio stream(s) 126 relative to prior sound characteristics, the example sound characteristic analyzer 202 identifies one or more sound events 204. For example, a sound event 204 can include an increase in amplitude of audio data followed by a decrease in the amplitude in the audio data. In some examples, the sound event(s) 204 are analyzed in view of reference sound data 208 by the example sound comparer 206 of FIG. 2 to classify the sounds event(s) 204 as, for example, expected sound event(s) 204 for the environment.

The example physiological data analyzer 210 accesses the physiological response data 130 collected from the user(s) exposed to sounds in the environment (block 304). The physiological response data 130 is obtained from the user(s) via the example sensor(s) 128 of the wearable device(s) 118 of FIG. 1. The physiological response data 130 can include, for example, heart rate data, respiration rate data, skin conductivity data, etc.

The example physiological data analyzer 210 identifies physiological event(s) 212 based on the physiological response data 130 (block 306). For example, the physiological data analyzer 210 identifies characteristics of and/or changes in one or more physiological parameters (e.g., heart rate, respiration rate, etc.) for the user(s). For example, the physiological data analyzer 210 can detect changes in a user's heart rate relative to a resting heart rate for the user. In some examples, the physiological data analyzer 210 identifies discrete or short-term physiological event(s) 212, such as an increase in heart rate followed by a return to a resting heart rate within a few minutes. In other examples, the physiological data analyzer 210 identifies long-term changes in a user's physiological responses, such as a sustained increase in the user's heart rate relative to a prior heart rate.

The example survey analyzer 222 accesses user input(s) 127 received at the sound impact analyzer 112 (block 308). The user input(s) 127 can include psychological survey response data received in response to, for example, survey(s) 134 presented to the user(s) (e.g., via the user device(s) 116). For example, the psychological survey response data can include responses indicating how the sound(s) made the user(s) feel (e.g., frightened). The user input(s) 127 can also include responses from the user(s) as to whether the user(s) heard a particular sound, whether the user(s) are wearing any noise reduction devices (e.g., ear plugs), etc.

The example correlation identifier 214 of the sound impact analyzer 112 analyzes the sound event(s) 204 relative to the physiological event(s) 212 for the user(s), the psychological survey response data, and/or other user input(s) 127 based on one or more supervised or unsupervised machine learning algorithms and, in some examples, the filter factor(s) 220 (block 310). The correlation identifier 214 uses the machine learning algorithms to identify correlations between the sound event(s) 204 and the physiological event(s) 212 to determine the physiological effects of sound in the environment on the user(s). The correlation identifier 214 can identify correlation(s) based on the correlation rule(s) 216, which can include known correlations (e.g., a sudden, loud sound raises a user's heart rate) or weighing factors (e.g., a rule that more weight should be given to sound event(s) having a long duration as compared to a short duration). The example correlation identifier 214 learns physiological response(s) to sound event(s) based on previously collected physiological response data 130 and previously generated audio stream(s) 126. The example correlation identifier 214 can identify correlations based on the learned physiological responses based on, for example, similar characteristics in the physiological response(s) and/or sound event(s) 204 currently being analyzed by the correlation identifier 214. In some examples, the correlation identifier 214 identifies correlation(s) between the sound event(s) 204 and the physiological event(s) 212 based on a time of occurrence of the sound event(s) 204 relative to a time of occurrence of the physiological event(s) 212 (e.g., event(s) 204, 212 that occur within a threshold time period of one another).

The example correlation identifier 214 can verify the correlations between the sound event(s) 204 and the physiological event(s) 212 based on the psychological survey response data analyzed by the survey analyzer 222. In some examples, the correlation identifier 214 determines that the sound event(s) 204 had a psychological effect on the user(s) based on the survey response data. The survey analyzer 222 tracks user survey responses over time and communicates with the correlation identifier 214 to track, for example, changes in a user's ability to hear sound(s) and/or changes in the user's psychological response to the sound over time (e.g., based on fright levels). In some examples, the correlation identifier adjust the correlation analysis based on user input(s) 127 (e.g., to accurately correlate a physiological and/or psychological response to a sound with a sound the user confirmed he or she heard).

In some examples, the analysis of the sound event(s) 204 and the physiological event(s) 212 by the correlation identifier 214 accounts for one or more filter factors 220 that may affect the identification of the correlation(s). For example, the filter adjuster 218 of the example sound impact analyzer 112 may determine that the audio data collected by a user device 116 is attenuated relative to audio data collected by another microphone enabled device in the environment (e.g., a stand-alone speaker/audio sensor device) and/or the reference sound data 208. Thus, the filter adjuster 218 determines that the audio data does not accurately represent the sound characteristics (e.g., amplitude levels) to which the user is exposed. In such examples, the correlation identifier 214 may adjust the correlation(s) to more accurately reflect the user's physiological and/or psychological responses to the sound event(s). In some examples, the filter adjuster 218 analyzes user input(s) 127 indicating that a user is wearing noise reduction device(s) (e.g., ear plugs). In such examples, correlation identifier 214 adjust may the correlation(s) to more accurately reflect the user's physiological and/or psychological responses to the sound event(s) in view of the effect(s) of the noise reduction device(s) on the user's hearing.

If the correlation identifier 214 identifies correlation(s) based on the sound event(s) 204, the physiological event(s) 212, the psychological survey response data, and/or other user input(s) 127 (block 312), the example report generator 226 of the example sound impact analyzer 112 generates one or more reports or instructions 136 (block 314). The report(s) 136 can include, for example, alert(s) to the user with respect to exposure to the sound and/or recommendations for audio levels based on the user's previous exposure to sound, physiological responses, and/or psychological responses. In some examples, the report(s) 136 include data regarding the user's hearing capabilities and/or other physiological parameters for delivery to the user and/or authorized medical personnel. In some examples, the report(s) 136 include data for a plurality of users in an environment with respect to physiological and/or psychological effects of sounds from the environment on the users. Such example report(s) 136 may be delivered to, for example, a building manager to evaluate noise sources from equipment in the building that are affecting multiple users, government agencies for regulation-making purposes, etc.

The report(s) 136 can include instruction(s) to reduce sound in the environment, such as an instruction for a machine to automatically reduce or end operations or for an audio playing device to automatically reduce a decibel level at which the audio is played. The report(s) 136 can include instruction(s) for an order for noise reduction device(s) (e.g., ear plugs) for the user(s) to be automatically placed via an online or local supplier (e.g., Amazon™). The report(s) 136 can include request(s) that are automatically transmitted to, for example, law enforcement, an employer, etc., based on the detection of a crowd-impact event (e.g., an explosion). The instruction(s) can be executed by the communicator 228 of the example sound impact analyzer 112 and/or communicated to one or more other processors (e.g., the processor 115 of the user device 116) for execution.

The example sound characteristic analyzer 202 of the example sound impact analyzer 112 continues to analyze the audio stream(s) 126 with respect to identifying sounds event(s) if the audio content stream(s) include additional audio data (block 316). If there is no further audio data in the audio stream(s) 126, the survey analyzer 222 determines whether further user input(s) 127 in response to, for example, survey(s) 134, have been received at the sound impact analyzer 112 (block 318). In some examples, the user(s) are surveyed about their psychological responses to the sound(s) after the audio data has been collected.

If there is no further audio data in the audio stream(s) 126 and no further user input(s) 127 are received by the sound impact analyzer 112, the example physiological data analyzer 210 determines whether there are further physiological event(s) 212 in the physiological response data 130 (block 320). In some examples, the physiological event(s) 212 do not appear in the physiological response data 130 until after the occurrence of the sound event(s) 204. For example, physiological changes such a sustained increased heart rate relative to a prior heart rate may occur over time as a result of repeated exposure to prolonged sounds (e.g., exposure to machine sounds during the work day). In some examples, the physiological event(s) occur after the user is removed from the environment. Therefore, the physiological data analyzer 210 continues to analyze physiological response data 130 received from the user(s) to identify physiological event(s) 212. Thus, the correlation identifier 214 can identify correlation(s) between sound event(s) and physiological event(s) based on proximity of the event(s) 204, 212 in time (e.g., a loud sound caused an increase in the user's heart rate at substantially the same time) and/or based on the detection of delayed or long-term physiological event(s) 212 that may still stem from exposure to the sound event(s) 204.

If there is no further audio data, no further psychological survey response data, and no further physiological response data to be analyzed, the instruction of FIG. 3 end (block 322).

Figure 4:
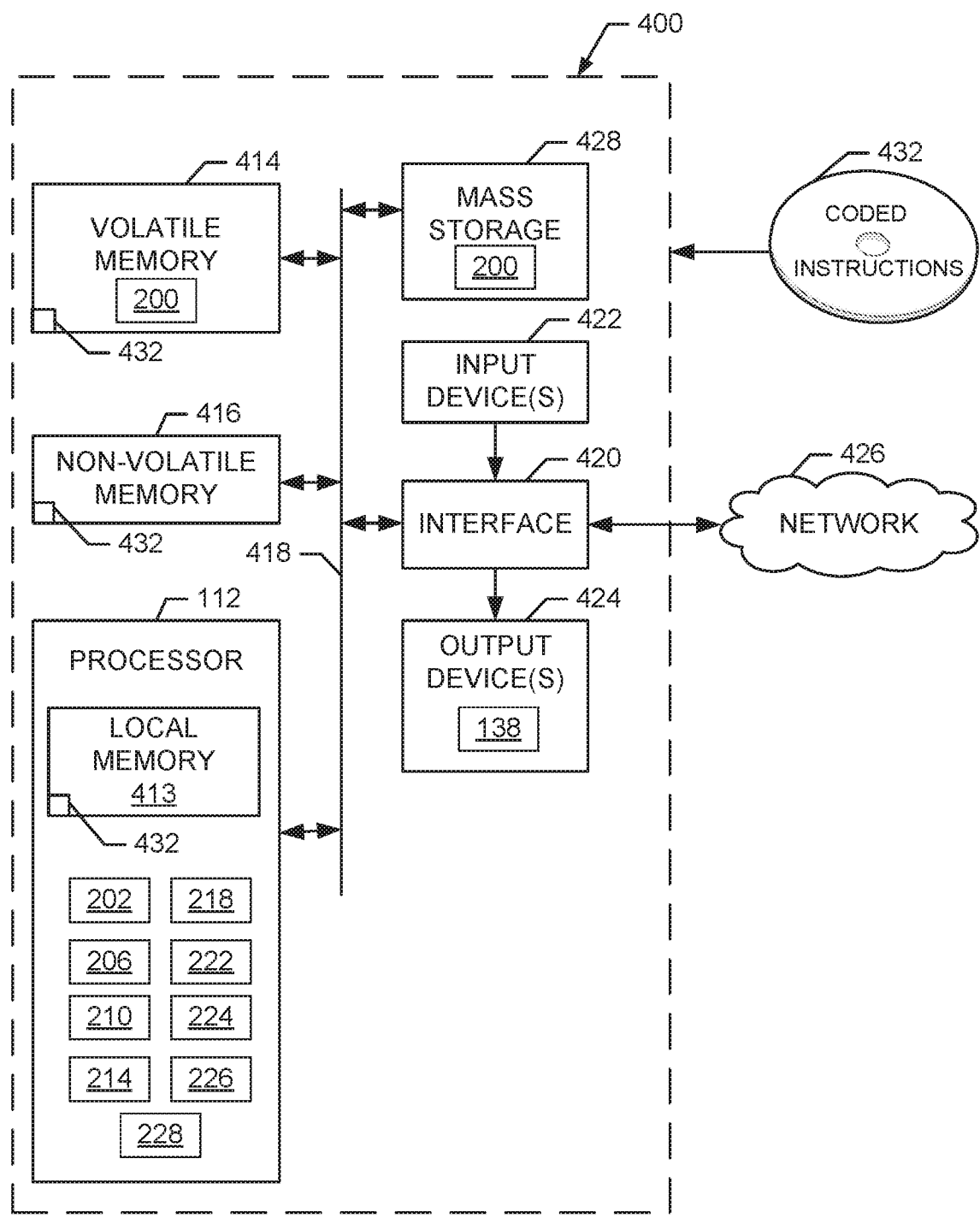
FIG. 4 illustrates an example processor platform that may execute the example instructions of FIG. 3 to implement example systems of FIGS. 1 and 2.

FIG. 4 is a block diagram of an example processor platform 400 capable of executing the instructions of FIG. 3 to implement the example sound impact analyzer 112 of FIGS. 1 and/or 2. The processor platform 400 can be, for example, a server, a personal computer, a mobile device (e.g., a cell phone, a smart phone, a tablet such as an iPad™), a personal digital assistant (PDA), an Internet appliance, a wearable device such as a watch, or any other type of computing device.

The processor platform 400 of the illustrated example includes a processor 112. The processor 112 of the illustrated example is hardware. For example, the processor 112 can be implemented by one or more integrated circuits, logic circuits, microprocessors or controllers from any desired family or manufacturer. In this example, the processor implements the sound impact analyzer and its components (e.g., the example sound characteristic analyzer 202, the example sound comparer 206, the example physiological data analyzer 210, the example correlation identifier 214, the example correlation identifier 214, the example filter adjuster 218, the example survey analyzer 222, the example crowd source analyzer 224, the example report generator 226, the example communicator 228).

The processor 112 of the illustrated example includes a local memory 413 (e.g., a cache). The processor 112 of the illustrated example is in communication with a main memory including a volatile memory 414 and a non-volatile memory 416 via a bus 418. The volatile memory 414 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 416 may be implemented by flash memory and/or any other desired type of memory device. Access to the main memory 414, 416 is controlled by a memory controller. The database 200 of the sound impact analyzer may be implemented by the main memory 414, 416.

The processor platform 400 of the illustrated example also includes an interface circuit 420. The interface circuit 420 may be implemented by any type of interface standard, such as an Ethernet interface, a universal serial bus (USB), and/or a PCI express interface.

In the illustrated example, one or more input devices 422 are connected to the interface circuit 420. The input device(s) 422 permit(s) a user to enter data and commands into the processor 112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 138, 424 are also connected to the interface circuit 420 of the illustrated example. The output devices 138, 424 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 420 of the illustrated example, thus, typically includes a graphics driver card, a graphics driver chip or a graphics driver processor. Reports of the report generator 226 may be exported on the interface circuit 420.

The interface circuit 420 of the illustrated example also includes a communication device such as a transmitter, a receiver, a transceiver, a modem and/or network interface card to facilitate exchange of data with external machines (e.g., computing devices of any kind) via a network 426 (e.g., an Ethernet connection, a digital subscriber line (DSL), a telephone line, coaxial cable, a cellular telephone system, etc.).

The processor platform 400 of the illustrated example also includes one or more mass storage devices 428 for storing software and/or data. Examples of such mass storage devices 428 include floppy disk drives, hard drive disks, compact disk drives, Blu-ray disk drives, RAID systems, and digital versatile disk (DVD) drives.

The coded instructions 432 of FIG. 3 may be stored in the mass storage device 428, in the volatile memory 414, in the non-volatile memory 1016, in the local memory 413, and/or on a removable non-transitory computer readable storage medium such as a CD or DVD.

From the foregoing, it will be appreciated that methods, systems, and apparatus have been disclosed to determine biological effects of sounds in an environment on individuals exposed to the environment. Disclosed examples analyze sound(s) collected from the environment via one or more microphones and physiological response data (e.g., heart rate data, respiration rate data) collected from the individuals exposed to the environment. In some examples, the analysis is performed by cloud-based devices to facilitate processing from multiple environments and/or multiple users. Disclosed examples identify efficiently correlations between the sound(s) and the physiological response data for an individual or across two or more individuals using machine learning algorithms. Disclosed example reduce errors in the correlations by accounting for factors that may affect the collection of the sound(s) and/or the user's exposure to the sound(s), such as placement of a microphone in a user's pocket, the resulting attenuation of the audio, and/or the use of noise reduction device(s) by the user.

Disclosed examples identify correlations between sound events and physiological events in view of physiological responses experienced by the user over time as a result of the exposure to the sound events. Thus, disclosed examples intelligently identify correlations that may not be directly time-based but, instead, are indicative of long-term or delayed physiological effects to exposure to the sounds. In some examples, users are surveyed about their experiences in view of exposure to sounds to assess, for example, psychological responses to the sounds or to track hearing ability over time. Based on the analysis, disclosed examples provide customized reports, alerts, etc. to the individuals and/or other authorized users (e.g., medical personnel, researchers, government agencies, etc.) with respect to exposure to sound(s) and the biological effects of the sound exposure on the users.

The following is a non-exclusive list of examples disclosed herein. Other examples may be included above. In addition, any of the examples disclosed herein can be considered in whole or in part, and/or modified in other ways.

Example 1 includes an apparatus including a sound characteristic analyzer to identify a sound event based on audio data collected in an environment. The apparatus includes a physiological data analyzer to identify a physiological event based on physiological response data collected from a user exposed to the sound event in the environment. The apparatus includes a correlation identifier to identify a correlation between the sound event and the physiological event and a report generator to generate a report based on the correlation.

Example 2 includes the apparatus as defined in example 1, wherein the sound characteristic analyzer is to identify the sound event based on a sound characteristic of the audio data.

Example 3 includes the apparatus as defined in example 2, wherein the sound characteristic includes one or more of amplitude, pitch, frequency, attack, or a duration of a sound in the audio data.

Example 4 includes the apparatus as defined in examples 1 or 2, wherein the physiological response data includes one or more of heart rate data, respiration rate data, blood pressure data, or skin conductivity data.

Example 5 includes the apparatus as defined in example 1, wherein the audio data is first audio data and the correlation identifier is to perform a comparison of the first audio data to second audio data and detect a change in a sound characteristic of the first audio data relative to the sound characteristic in the second audio data, the correlation identifier to identify the correlation based on the change in the characteristic.

Example 6 includes the apparatus as defined in example 5, wherein the correlation identifier is to identify an attenuation or a gain of the first audio data relative to the second audio data and adjust the correlation based on the attenuation or the gain.

Example 7 includes the apparatus as defined in of any of examples 1, 5, or 6, further including a filter adjuster to analyze a user input indicating that the user employs a noise reduction device.

Example 8 includes the apparatus as defined in examples 1 or 2, further including a survey analyzer to perform a comparison of the correlation to a user input, the user input associated with the sound event and verify the correlation based on the comparison.

Example 9 includes the apparatus as defined in any of examples 1, 2, or 5, wherein the user is a first user, the physiological event is a first physiological event, and the correlation is a first correlation, the correlation identifier to identify a second correlation between the sound event and a second physiological event associated with a second user different from the first user.

Example 10 includes the apparatus as defined in example 9, wherein the report generator is to generate a first report based on the first correlation and a second report based on the second correlation.

Example 11 includes the apparatus as defined in example 10, wherein at least one of the first report or the second report includes a sound exposure alert for the user based on the correlation.

Example 12 includes the apparatus as defined in example 9, further including a sound comparer to perform a comparison of the sound event to a reference sound event and a crowd source analyzer to identify the sound event as affecting the first user and the second user based on the first correlation, the second correlation, and the comparison.

Example 13 includes the apparatus as defined in example 9, wherein the report generator is to transmit a request to a third party based on the identification of the sound event as affecting the first user and the second user.

Example 14 includes the apparatus as defined in any of examples 1, 2, or 5, wherein the sound event occurs at a first time and the physiological event occurs at a second time, the second time occurring after the first time.

Example 15 includes the apparatus as defined in any of examples 1, 2, or 5, wherein the user is a first user, the correlation identifier to identify the correlation based on previously collected physiological response data for the first user or for a second user.

Example 16 includes the apparatus as defined in example 15, wherein the correlation identifier is to identify the correlation based on a trend identified in first previously collected physiological response data for the first user and second previously collected physiological response data for the second user relative to the sound event.

Example 17 includes the apparatus as defined in example 1, wherein the report generator is to automatically place an order for a noise reduction device for the user.

Example 18 includes a method including identifying, by executing an instruction with a processor, a sound in an audio stream collected in an environment. The method includes identifying, by executing an instruction with the processor, a physiological event based on physiological response data collected from a user exposed to the sound in the environment. The method includes determining, by executing an instruction with the processor, a correlation between the sound and the physiological event. The method includes generating, by executing an instruction with the processor, a report based on the correlation.

Example 19 includes the method as defined in example 18, further including identifying the sound based on a sound characteristic of data in the audio stream.

Example 20 includes the method as defined in example 19, wherein the sound characteristic includes one or more of amplitude, pitch, frequency, attack, or a duration of a sound in the data.

Example 21 includes the method as defined in examples 18 or 19, wherein the physiological response data includes one or more of heart rate data, respiration rate data, blood pressure data, or skin conductivity data.

Example 22 includes the method as defined in example 18, wherein the audio stream is a first audio stream and further including performing a comparison of the first audio stream to a second audio stream. The method includes detecting a change in a sound characteristic of the first audio stream relative to the sound characteristic in the second audio stream. The method includes identifying the correlation based on the change in the characteristic.

Example 23 includes the method as defined in example 22, wherein the sound characteristic is a decibel level and further including measuring a first decibel level of the first audio stream and a second decibel level of the second audio stream. The method includes identifying an attenuation or a gain of the first decibel level relative to the second decibel level. The method includes adjusting the correlation based on the attenuation or the gain.

Example 24 includes the method as defined in any of examples 18, 22, or 23, further including analyzing a user input indicating that the user employs a noise reduction device and adjusting the correlation based on the user input.

Example 25 includes the method as defined in examples 18 or 19, further including verifying the correlation based on a user input received in response to the sound.

Example 26 includes the method as defined in any of examples 18, 19, or 22, wherein the user is a first user, the physiological event is a first physiological event, and the correlation is a first correlation, further including identifying a second correlation between the sound and a second physiological event associated with a second user different from the first user.

Example 27 includes the method as defined in example 26, wherein generating the report includes generating a first report based on the first correlation and a second report based on the second correlation.

Example 28 includes the method as defined in example 27, wherein at least one of the first report or the second report includes an instruction for a sound generating device to reduce an amplitude of the sound.

Example 29 includes the method as defined in example 26, further including performing a comparison of the sound to a reference sound and identifying the sound as affecting the first user and the second user based on the first correlation, the second correlation, and the comparison.

Example 30 includes the method as defined in example 26, further including transmitting a request to a third party based on the identification of the sound as affecting the first user and the second user.

Example 31 includes the method as defined in any of examples 18, 19, or 22, wherein the sound occurs at a first time and the physiological event occurs at a second time, the second time occurring after the first time.

Example 32 includes the method as defined in any of examples 18, 19, or 22, wherein the user is a first user and further including identifying the correlation based on previously collected physiological response data for the first user or for a second user.

Example 33 includes the method as defined in example 32, further including identifying the correlation based on a trend identified in first previously collected physiological response data for the first user and second previously collected physiological response data for the second user relative to the sound.

Example 34 includes the method as defined in example 18, wherein generating the report includes automatically placing an order for a noise reduction device for the user.

Example 35 includes at least one computer readable storage medium comprising instructions that, when executed, cause a machine to at least detect a sound event in audio data collected in an environment, detect a physiological event in physiological response data collected from a user exposed to the sound event in the environment, identify a correlation between the sound event and the physiological event, and generate an instruction based on the correlation.

Example 36 includes the at least one computer readable storage medium as defined in example 35, wherein the instructions, when executed, further cause the machine to identify the sound event based on a sound characteristic of the audio data.

Example 37 includes the at least one computer readable storage medium as defined in example 36, wherein the sound characteristic includes one or more of amplitude, pitch, frequency, attack, or a duration of a sound in the audio data.

Example 38 includes the at least one computer readable storage medium as defined in examples 35 or 36, wherein the physiological response data includes one or more of heart rate data, respiration rate data, blood pressure data, or skin conductivity data.

Example 39 includes the at least one computer readable storage medium as defined in example 35, wherein the audio data is first audio data and instructions, when executed, further cause the machine to perform a comparison of the first audio data to second audio data, detect a change in a sound characteristic of the first audio data relative to the sound characteristic in the second audio data, and identify the correlation based on the change in the characteristic.

Example 40 includes the at least one computer readable storage medium as defined in example 39, wherein the instructions, when executed, further cause the machine to identify an attenuation or a gain of the first audio data relative to the second audio data and adjust the correlation based on the attenuation or the gain.

Example 41 includes the at least one computer readable storage medium as defined in any of examples 35, 39, or 40, wherein the instructions, when executed, further cause the machine to analyze a user input indicating that the user employs a noise reduction device and adjust the correlation based on the user input.

Example 42 includes the at least one computer readable storage medium as defined in examples 35 or 36, wherein the instructions, when executed, further cause the machine to verify the correlation based on a user input associated with the sound event.

Example 43 includes the at least one computer readable storage medium as defined in any of examples 35, 36, or 39, wherein the user is a first user, the physiological event is a first physiological event, and the correlation is a first correlation, and wherein the instructions, when executed, further cause the machine to identify a second correlation between the sound event and a second physiological event associated with a second user different from the first user.

Example 44 includes the at least one computer readable storage medium as defined in example 43, wherein the instructions, when executed, further cause the machine to generate a first instruction based on the first correlation and a second instruction based on the second correlation.

Example 45 includes the at least one computer readable storage medium as defined in example 44, wherein at least one of the first instruction or the second instruction includes an instruction for a sound generating device to reduce an amplitude of the sound.

Example 46 includes the at least one computer readable storage medium as defined in example 45, wherein the instructions, when executed, further cause the machine to perform a comparison of the sound event to a reference sound event and determine that the sound event affects the first user and the second user based on the first correlation, the second correlation, and the comparison.

Example 47 includes the at least one computer readable storage medium as defined in example 44, wherein the instructions, when executed, further cause the machine to generate the instruction by transmitting a request to a third party based on the identification of the sound event as affecting the first user and the second user.

Example 48 includes the at least one computer readable storage medium as defined in any of examples 35, 36, or 39, wherein the sound event occurs at a first time and the physiological event occurs at a second time, the second time occurring after the first time.

Example 49 includes the at least one computer readable storage medium as defined in any of examples 35, 36, or 39, wherein the user is a first user and wherein the instructions, when executed, further cause the machine to identify the correlation based on previously collected physiological response data for the first user or for a second user.

Example 50 includes the at least one computer readable storage medium as defined in example 49, wherein the instructions, when executed, further cause the machine to identify the correlation based on a trend identified in first previously collected physiological response data for the first user and second previously collected physiological response data for the second user relative to the sound event.

Example 51 includes the at least one computer readable storage medium as defined in example 35, wherein the instructions, when executed, further cause the machine to generate the instruction by automatically placing an order for a noise reduction device for the user.

Example 52 includes an apparatus including means for identifying a sound event based on audio data collected in an environment, means for identifying a physiological event based on physiological response data collected from a user exposed to the sound event in the environment, means for identifying a correlation between the sound event and the physiological event, and means for generating an instruction based on the correlation.

Example 53 includes the apparatus as defined in claim 52, wherein the instruction includes one or more of an order for a noise reduction device for the user, a command for a sound generating device to reduce an amplitude of the sound, or an alert for a third party.

Example 54 includes the apparatus as defined in claim 52, wherein the audio data is first audio data and further including means for identifying an attenuation of the first audio data relative to second audio data, the means for identifying the correlation to adjust the correlation based on the attenuation.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method comprising:
   identifying, by executing an instruction with a processor, a first sound and a second sound in an audio stream collected in an environment, the first sound generated by a sound generating device;
   identifying, by executing an instruction with the processor, a physiological event based on physiological response data collected from a user exposed to the first sound and the second sound in the environment in a first time period;
   assigning, by executing an instruction with the processor, a weighing factor to the first sound based on a first attack characteristic of the first sound in the first time period relative to a first attack characteristic of the second sound in the first time period;
   determining, by executing an instruction with the processor, a correlation between the first sound and the physiological event based on the weighing factor; and
   instructing, by executing an instruction with the processor, the sound generating device to adjust the first attack characteristic or a second characteristic of the first sound in response to the correlation.

2. The method as defined in claim 1, wherein the audio stream is a first audio stream and further including:
   performing a comparison of the first audio stream to a second audio stream;
   detecting a change in the first attack characteristic of the first sound in the first audio stream relative to the first attack characteristic of the first sound in the second audio stream; and
   identifying the correlation based on the change in the first attack characteristic.

3. The method as defined in claim 1, wherein the user is a first user, the physiological event is a first physiological event, and the correlation is a first correlation, and further including:
   identifying a second correlation between (a) one of the first sound or the second sound and (b) a second physiological event associated with a second user different from the first user; and
   generating a first report based on the first correlation and generating a second report based on the second correlation.

4. The method as defined in claim 1, wherein the user is a first user and further including identifying the correlation based on previously collected physiological response data for the first user or for a second user.

5. The method as defined in claim 1, wherein instructing the sound generating device to adjust the second characteristic of the first sound includes instructing the sound generating device to reduce an amplitude of the first sound.

6. The method of claim 1, further including adjusting the correlation based on a filter factor associated with a variable affecting one or more of the collection of the audio stream or exposure of the user to the first sound.

7. The method of claim 1, wherein the second characteristic of the first sound includes a duration of the first sound.

8. The method of claim 1, further including:
   classifying the first sound as an expected sound or an unexpected sound; and
   determining the correlation based on the classification of the first sound.

9. At least one computer readable storage medium comprising instructions that, when executed, cause a machine to at least:
   detect a first sound event and a second sound event in audio data, the audio data corresponding to audio collected in an environment, the first sound event to be generated by a sound generating device;
   detect a physiological event in physiological response data collected from a user exposed to the first sound event and the second sound event in the environment in a first time period;
   assign a weighing factor to the first sound event based on a first sound characteristic of the first sound event relative to a first sound characteristic of the second sound event, the first sound characteristic of the first sound event corresponding to an attack characteristic of the first sound event in the first time period, the first sound characteristic of the second sound event corresponding to an attack characteristic of the second sound event in the first time period;
   identify a correlation between the first sound event and the physiological event based on the weighing factor; and
   transmit a first request to the sound generating device in response to the correlation, the first request to cause the sound generating device to adjust the audio.

10. The at least one computer readable storage medium as defined in claim 9, wherein the instructions, when executed, further cause the machine to detect the first sound event based on one or more of amplitude, pitch, frequency, or a duration of a sound in the audio data.

11. The at least one computer readable storage medium as defined in claim 9, wherein the audio data is first audio data and wherein the instructions, when executed, further cause the machine to:
   perform a comparison of the first audio data to second audio data;
   detect a change in the first sound characteristic of the first sound event in the first audio data relative to the first sound characteristic of the first sound event in the second audio data; and
   identify the correlation based on the change in the first sound characteristic.

12. The at least one computer readable storage medium as defined in claim 11, wherein the instructions, when executed, further cause the machine to identify an attenuation or a gain of the first audio data relative to the second audio data and adjust the correlation based on the attenuation or the gain.

13. The at least one computer readable storage medium as defined in claim 9, wherein the instructions, when executed, further cause the machine to:
   analyze a user input indicating that the user employs a noise reduction device; and
   adjust the correlation based on the user input.

14. The at least one computer readable storage medium as defined in claim 9, wherein the user is a first user, and wherein the instructions, when executed, further cause the machine to identify the correlation based on previously collected physiological response data for the first user or for a second user.

15. The at least one computer readable storage medium as defined in claim 9, wherein the instructions, when executed, further cause the machine to automatically place an order for a noise reduction device for the user.

16. The at least one computer readable storage medium as defined in claim 9, wherein the instructions, when executed, further cause the machine to detect the first sound event based on the first sound characteristic of the first sound event or a second sound characteristic of the first sound event.

17. The at least one computer readable storage medium as defined in claim 9, wherein the physiological response data includes one or more of heart rate data, respiration rate data, blood pressure data, or skin conductivity data.

18. The at least one computer readable storage medium as defined in claim 9, wherein the instructions, when executed, further cause the machine to verify the correlation based on a user input associated with the first sound event.

19. The at least one computer readable storage medium as defined in claim 9, wherein the user is a first user, the physiological event is a first physiological event, and the correlation is a first correlation, and wherein the instructions, when executed, further cause the machine to identify a second correlation between (a) one of the first sound event or the second sound event and (b) a second physiological event associated with a second user different from the first user.

20. The at least one computer readable storage medium as defined in claim 19 wherein the first request is to cause the sound generating device to reduce an amplitude of the audio.

21. The at least one computer readable storage medium as defined in claim 19, wherein the instructions, when executed, further cause the machine to:
   perform a comparison of the first sound event to a reference sound event; and
   determine that the first sound event affects the first user and the second user based on the first correlation, the second correlation, and the comparison.

22. The at least one computer readable storage medium as defined in claim 21, wherein the instructions, when executed, further cause the machine to transmit a second request to a third party based on the determination of the first sound event as affecting the first user and the second user.

23. The at least one computer readable storage medium as defined in claim 9, wherein the instructions, when executed, further cause the machine to adjust the correlation based on a filter factor associated with a variable affecting one or more of the collection of the audio data or exposure of the user to the first sound event.

24. The at least one computer readable storage medium as defined in claim 9, wherein the instructions, when executed, further cause the machine to:
   classify the first sound event as an expected sound event or an unexpected sound event; and
   identify the correlation based on the classification of the first sound event.

25. The at least one computer readable storage medium as defined in claim 9, wherein the first request is to cause the sound generating device to adjust a duration of the first sound event.

26. An apparatus comprising:
   at least one memory;
   machine-readable instructions; and
   processor circuitry to execute the machine-readable instructions to:
      detect a first sound event and a second sound event in audio data, the audio data corresponding to audio collected in an environment, the first sound event to be generated by a sound generating device;
      detect a physiological event in physiological response data collected from a user exposed to the first sound event and the second sound event in the environment in a first time period;
      assign a weighing factor to the first sound event based on a first sound characteristic of the first sound event relative to a first sound characteristic of the second sound event, the first sound characteristic of the first sound event corresponding to an attack characteristic of the first sound event in the first time period, the first sound characteristic of the second sound event corresponding to an attack characteristic of the second sound event in the first time period;
      identify a correlation between the first sound event and the physiological event based on the weighing factor; and
      transmit a first request to the sound generating device in response to the correlation, the first request to cause the sound generating device to adjust the audio.

27. The apparatus as defined in claim 26, wherein the processor circuitry is to detect the first sound event based on one or more of amplitude, pitch, frequency, or a duration of a sound in the audio data.

28. The apparatus as defined in claim 26, wherein the audio data is first audio data and wherein the processor circuitry is to:
   perform a comparison of the first audio data to second audio data;
   detect a change in the first sound characteristic of the first sound event in the first audio data relative to the first sound characteristic of the first sound event in the second audio data; and
   identify the correlation based on the change in the first sound characteristic.

29. The apparatus as defined in claim 28, wherein the processor circuitry is to identify an attenuation or a gain of the first audio data relative to the second audio data and adjust the correlation based on the attenuation or the gain.

30. The apparatus as defined in claim 26, wherein the processor circuitry is to:
   analyze a user input indicating that the user employs a noise reduction device; and
   adjust the correlation based on the user input.

31. The apparatus as defined in claim 26, wherein the user is a first user, and the processor circuitry is to identify the correlation based on previously collected physiological response data for the first user or for a second user.

32. The apparatus as defined in claim 26, wherein the processor circuitry is to automatically place an order for a noise reduction device for the user.

33. The apparatus as defined in claim 26, wherein the processor circuitry is to detect the first sound event based on the first sound characteristic of the first sound event or a second sound characteristic of the first sound event.

34. The apparatus as defined in claim 26, wherein the physiological response data includes one or more of heart rate data, respiration rate data, blood pressure data, or skin conductivity data.

35. The apparatus as defined in claim 26, wherein the processor circuitry is to verify the correlation based on a user input associated with the first sound event.

36. The apparatus as defined in claim 26, wherein the user is a first user, the physiological event is a first physiological event, the correlation is a first correlation, and wherein the processor circuitry is to identify a second correlation between (a) one of the first sound event or the second sound event and (b) a second physiological event associated with a second user different from the first user.

37. The apparatus as defined in claim 36 wherein the first request is to cause the sound generating device to reduce an amplitude of the audio.

38. The apparatus as defined in claim 36, wherein the processor circuitry is to:

perform a comparison of the first sound event to a reference sound event; and determine that the first sound event affects the first user and the second user based on the first correlation, the second correlation, and the comparison.

39. The apparatus as defined in claim 38, wherein the processor circuitry is to transmit a second request to a third party based on the determination of the first sound event as affecting the first user and the second user.

40. The apparatus as defined in claim 26, wherein the processor circuitry is to adjust the correlation based on a filter factor associated with a variable affecting one or more of the collection of the audio data or exposure of the user to the first sound event.

41. The apparatus as defined in claim 26, wherein the first request is to cause the sound generating device to adjust a duration of the first sound event.

42. The apparatus as defined in claim 26, wherein the processor circuitry is to:

classify the first sound event as an expected sound event or an unexpected sound event; and identify the correlation based on the classification of the first sound event.

\* \* \* \* \*